United States Patent [19]

Miyamae

[11] Patent Number: 4,776,333

[45] Date of Patent: Oct. 11, 1988

[54] VENTILATOR WITH VARIABLE FLOW PATTERN

[75] Inventor: Ruichi Miyamae, Osaka, Japan

[73] Assignee: Sharp Kabushiki Kaisha, Osaka, Japan

[21] Appl. No.: 119,264

[22] Filed: Nov. 9, 1987

Related U.S. Application Data

[63] Continuation of Ser. No. 697,390, Feb. 1, 1985, abandoned.

[30] Foreign Application Priority Data

Feb. 2, 1984 [JP] Japan .............................. 59-14222[U]

[51] Int. Cl.$^4$ ............................................ A61M 16/00
[52] U.S. Cl. ................................................ 128/204.21
[58] Field of Search ....................... 128/203.12, 203.25, 128/204.21, 205.12, 204.22, 204.23, 203.14, 205.24; 137/624.11, 624.13

[56] References Cited

U.S. PATENT DOCUMENTS

| | | |
|---|---|---|
| 2,830,579 | 10/1952 | Saklad et al. . |
| 3,741,208 | 6/1973 | Jonsson et al. . |
| 3,961,627 | 6/1976 | Ernst et al. . |
| 4,001,700 | 1/1977 | Cook et al. ...................... 128/204.21 |
| 4,036,221 | 7/1977 | Hillsman et al. ................ 128/204.23 |
| 4,206,754 | 6/1980 | Cox et al. ........................ 128/204.21 |
| 4,323,064 | 4/1982 | Hoenig et al. . |
| 4,345,612 | 8/1982 | Koni et al. ...................... 128/204.21 |
| 4,357,936 | 11/1982 | Ellestad et al. ................. 128/204.23 |
| 4,393,869 | 7/1983 | Boyarsky et al. ............... 128/204.21 |
| 4,471,773 | 9/1984 | Bunnell et al. ................. 128/204.21 |
| 4,527,557 | 7/1985 | DeVries et al. ................ 128/204.23 |

FOREIGN PATENT DOCUMENTS 2301967 10/1976 France ............................ 128/204.21

OTHER PUBLICATIONS

Barbini, "IPPV Flow Pattern Optimization By Using Computer Technique", 1980, IEEE, pp. 277-281.

Primary Examiner—Edward M. Coven
Assistant Examiner—J. P. Lacyk
Attorney, Agent, or Firm—Birch, Stewart, Kolasch & Birch

[57] ABSTRACT

An improved artificial ventilator is capable of selection or setting of any arbitrary pattern or waveform of the flow rate of inspiration gas. The flow rate of inspiration gas is controlled through an inspiration valve according to an input representative of a flow rate pattern of an inspiration gas with the aid of a micro-computer, whereby a desired flow pattern of inspiration gas is optionally set.

9 Claims, 4 Drawing Sheets

VENTILATOR WITH VARIABLE FLOW PATTERN

This application is a continuation of application Ser. No. 697,390 filed on Feb. 1, 1985, now abandoned.

BACKGROUND OF THE INVENTION

This invention relates to an improvement in an artificial ventilator for medical use.

Some artificial ventilators for medical use have a device for selection of inspiration flow according to the condition of the patient especially the lungs or trachea of the patient. Conventional ventilators have only one fixed flow pattern or at most provide a choice of two to four flow patterns. Though in the latter there are, for example, constant flow, increasing flow and decreasing flow and sine flow available for the operators' use, it is not necessarily possible to offer optimum inspiration operation for various conditions of the patient.

OBJECT AND SUMMARY OF THE INVENTION

Accordingly, it is an object of the present invention to provide an improved artificial ventilator which is capable of selecting or setting any arbitrary pattern or waveform of the flow rate of inspiration gas.

It is another object of the present invention to provide an artificial ventilator wherein the flow rate of inspiration gas is controlled according to an input representative of a desired flow rate pattern of an inspiration gas, which ventilator is provided with means for optionally setting a desired flow pattern of inspiration gas.

BRIEF DESCRIPTION OF THE DRAWINGS

Other objects and many of the attendant advantages of the present invention will be easily appreciated as the same becomes better understood by reference to the following detailed description in conjunction with the accompanying drawings in which like reference numerals designate like part throughout the figures thereof, and wherein.

DETAILED DESCRIPTION OF THE INVENTION

Figure 1:
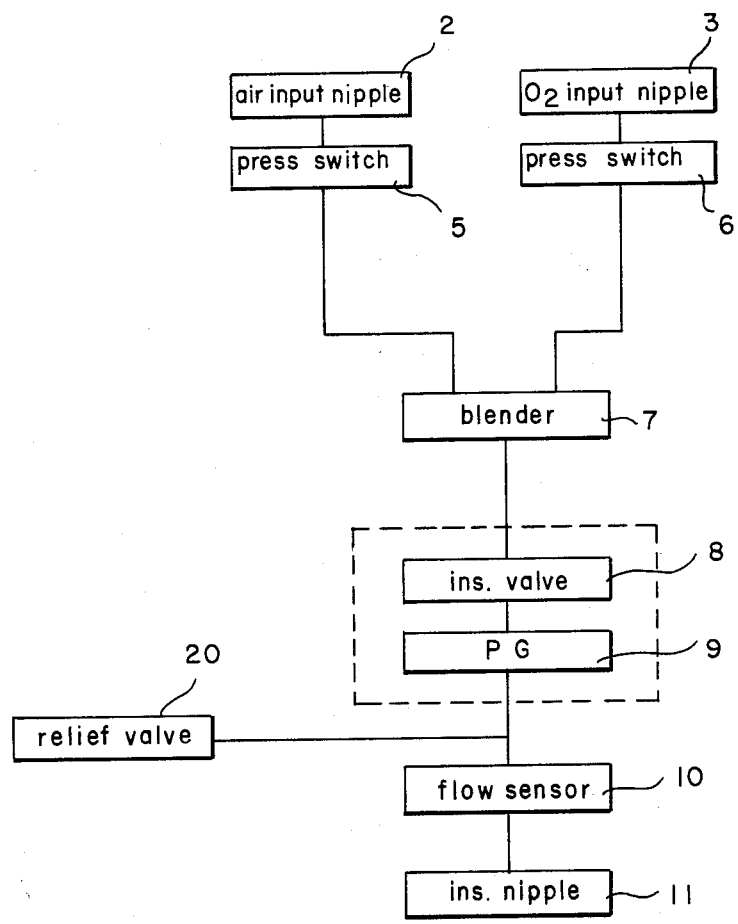
FIG. 1 is a schematic block diagram of an artificial ventilator according to an embodiment of the present invention.

Referring to FIG. 1, there is illustrated an inspiration gas circuit in an artificial ventilator according to an embodiment of the present invention. The design of the ventilator illustrated is that, to constantly keep a preset ventilation condition, a micro-computer (shown in FIG. 2 as 32) constantly monitors electric signals from an inspiration flow sensor in an inspiration circuit, an expiration flow sensor and an inspiration trigger sensor and makes appropriate decisions and effects appropriate processes. The micro-computer sends control signals to an inspiration valve and an expiration valve to maintain the volume of ventilation and control respiration cycle and the waveform of inspiration flow rate. In FIG. 1, air and oxygen ($O_2$) are introduced through gas inlet nipples 2 and 3. Pressure switches 5 and 6 are provided for each of the input portions. Air and oxygen input portions of a blender or mixer 7 are provided with a gas filter. The blender is manifolded so that gases running through the filters enter respective regulation valves. The function of the regulation valves is to not only determine the pressure in the inspiration circuit but also reduce to a minimum the variation in the oxygen density against varying gas source pressure. By rotation of an oxygen density select knob, a needle valve in the blender operates to set the oxygen density at a desired level through variation in its opening. To make a decision as to input gas alarm and to compensate for flow sensors, sprockets and a conveyor belt affixed to the shaft of the knob of the blender varies a potentiometer. For example, the oxygen density is adjustable between 21 and 100% with a rotation angle of the blender knob ranging up to 300°.

Mixture of air and oxygen gas from the blender output is fed to a direct drive inspiration valve 8 for opening and closing of the inspiration circuit. The use of the direct valve aims at enhancement of the inspiration response speed of the inspiration trigger. The inspiration gas is then fed to a flow rate control valve or pulse generator 9. The pulse generator 9 plays an important role in the present invention and controls a flow rate pattern of the inspiration gas. More particularly, the pulse generator is of a needle type wherein a cam is driven with a pulse motor under control by signals from a central processing unit (CPU) of the micro-computer. A relief valve 20 enables the inspiration gas to escape therethrough to avoid the risk of harm to the patient when the pressure in the inspiration circuit exceeds a given value.

An inspiration flow sensor 10 measures the flow rate of the inspiration gas and is typically of the hot-wire type. The inspiration gas is sent from an inspiration nipple 11 to the patient by way of a patient hose. An oxygen ($O_2$) sensor nipple is also provided for supplying a sampling gas to an oxygen ($O_2$) sensor.

Figure 2:
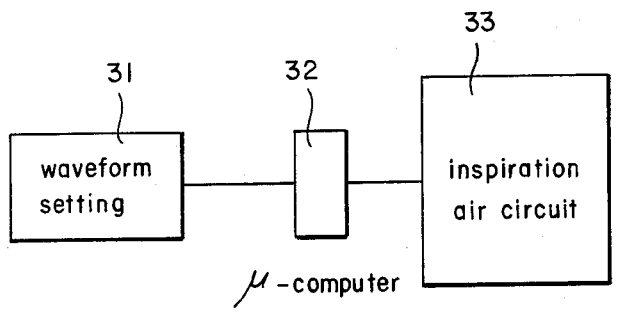
FIG. 2 is a schematic illustration of a waveform setting means used with an artificial ventilator according to an embodiment of the present invention.

FIG. 2 is a schematic view of the flow pattern setting device in the inspiration circuit according to the present invention. A waveform setting means 31 comprises an inspiration gas flow pattern setting means. An inspiration flow pattern set with the waveform setting means 31 is sent in the form of electric signals to the micro-computer (which functions as control means) 32 electrically connected to the waveform setting means 31. The micro-computer 32 controls the inspiration circuit in response to the signals so as to control input and output of the gas according to the inspiration flow pattern.

Figure 3:
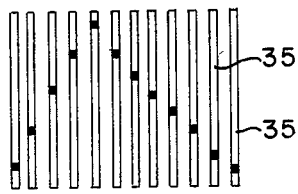
FIG. 3 illustrates the arrangement of the slide volume potentiometer used in the waveform setting means of FIG. 2.

The waveform setting means (31 of FIG. 2), as illustrated in FIG. 3, comprises a given number (typically, 12) of slide volume potentiometer 35 arranged in parallel with one another. Each lever of the slide volume potentiometers is designated by the black circle. Provided that a desired pattern is set with the given number of slide volume potentiometers 35 as illustrated, an optimum distribution of the inspiration gas is provided according to the waveform or flow pattern which is most appropriate for the conditions of individual patients especially given the condition of their lungs and trachea or the dynamic condition of the circulation system.

Figure 5:
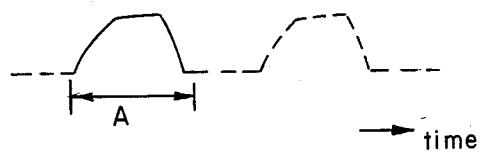
FIG. 5 is an inspiration flow pattern waveform for explanation of flow rate control setting means.
Figure 4:
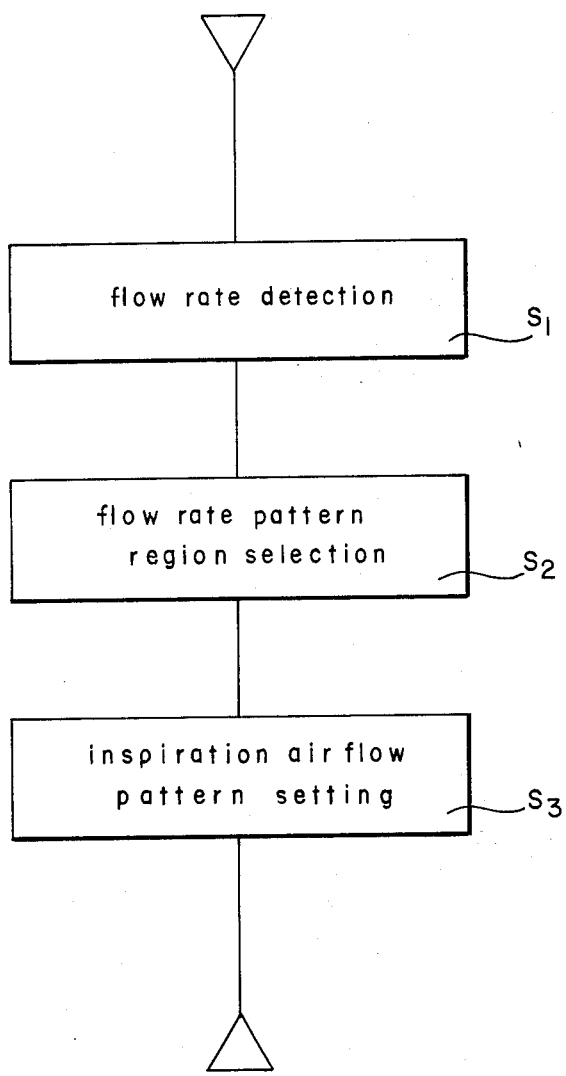
FIG. 4 is a flow chart explaining the flow chart used by the inspiration circuit in one embodiment of the present invention.

Should the patient be able to breath unaided, as shown in the flow chart of FIG. 4, the flow sensor 10 in the inspiration circuit 33 senses flow rate (step $S_1$) and a display (CRT, etc.) displays the selected flow pattern. With a cursor specifying a region of the flow pattern (step $S_2$, A shows the location of the cursor in FIG. 5), that region is used as an inspiration flow pattern during auxiliary or regulatory respiration (step $S_3$). It is obvious in the art that the waveform setting means as shown in FIG. 3 may be replaced with an appropriate alternative.

Figure 6:
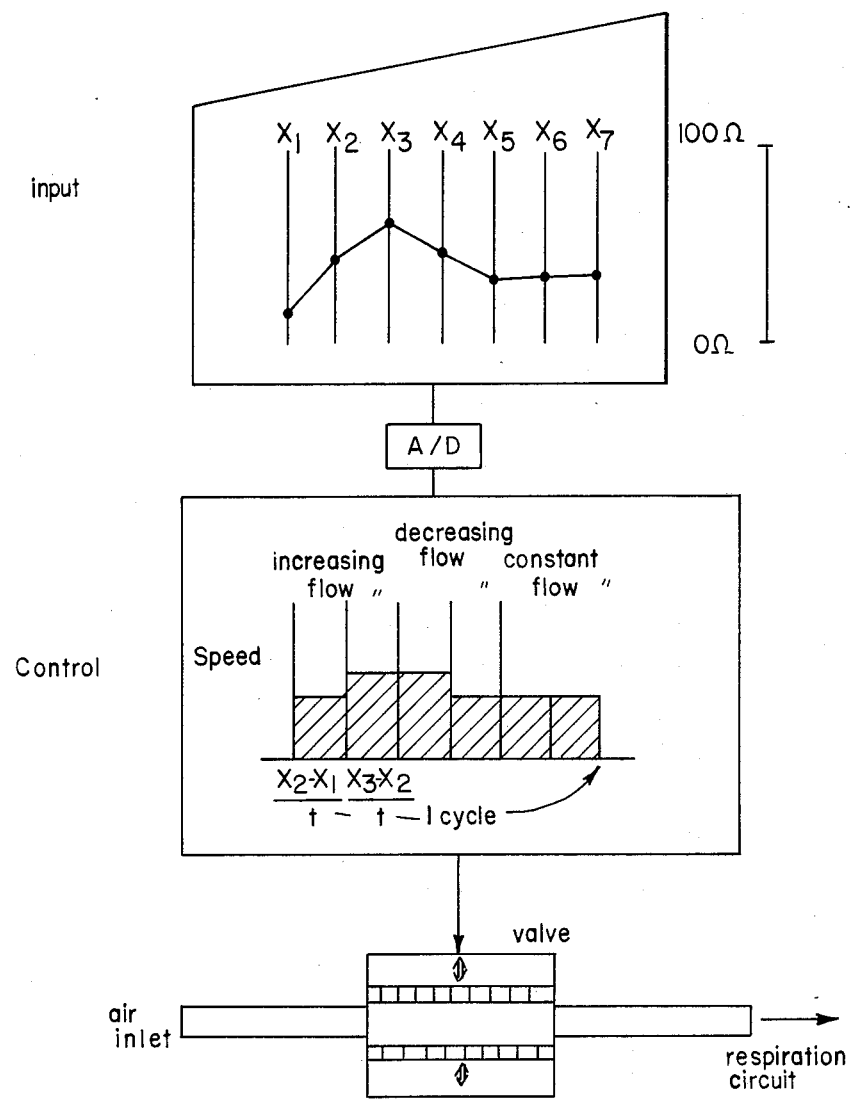
FIG. 6 schematically illustrates in more detail the flow pattern setting device according to the present invention.

FIG. 6 schematically illustrates in more detail the flow pattern setting device according to the present invention. The input means 31, as seen from FIG. 3, includes the given number of variable resistors ranging from 0 to 100 ohms, for example. The input means is connected through an analog-to-digital converter to the control means 32 and sets up a control cycle of operation, which in the present example consists of two flow increasing steps, two flow decreasing steps and two constant flow steps as illustrated in FIG. 6. Electric signals indicative of the respective steps are generated from the micro-computer 32 and fed to the electro-magnetic inspiration valve 8.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A control system for an artificial ventilator having a variable gas flow rate during a patient's inspiration comprising:
   input means for introducing flow rate information; and
   means, responsive to said flow rate information developed by said input means, for controlling the rate of said gas flow to match the flow rates introduced by said flow rate information;
   said input means introducing said flow rate information as a plurality of volumes distributed over the time of a single inspiration to allow introduction of time related flow rate information, said input means includes a plurality of sliding flow rate selection means, disposed so as to slide in parallel patterns, for introducing said flow rate information, each said flow rate selection means introducing a volume for a particular time period of a said inspiration, each said flow selection means having an indicator, the position of which indicates the relative flow rate for its associated time period of said inspiration, the indicators of said flow rate selection means collectively forming points above a reference line defining a curve which represents the flow rate with respect to time of said flow rate information for said inspiration.

2. The ventilator of claim 1 wherein said indicators are levers of said flow rate selection means.

3. A method of controlling an artificial ventilator having a variable gas flow rate during a patient's inspiration comprising:
   introducing flow rate information as a plurality of volumes distributed over the time of a single inspiration; and
   controlling the gas flow of said ventilator so as to match the flow rate of said ventilator with the flow rate of said flow rate information at a corresponding time during said inspiration; and
   monitoring the flow rate of a patient's inspiration while the patient breathes unaided;
   wherein said flow rate information introduced is indicative of the patient's unaided flow rate at a plurality of points in time distributed during the patient's inspiration.

4. The method of claim 3 wherein said step of introducing utilizes a plurality of sliding volume selection means, each corresponding to the volume at an instant of time during said inspiration, said step of introducing including positioning each said sliding volume selection means to indicate the rate of said gas flow for its corresponding instant in time during said inspiration.

5. An artificial ventilator comprising:
   an inspiration gas circuit;
   means for introducing an input representative of a flow rate pattern of an inspiration gas wherein said input corresponds to a plurality of volumes to be distributed over the time of a single inspiration, said volumes over time constituting said flow rate pattern;
   computer means for providing a control cycle of operation in response to said input from said means for introducing, said control cycle of operation comprising a flow increasing step, a flow decreasing step and a flow constant step;
   valve means for controlling the flow rate of the inspiration gas in response to said control cycle of operation from said computer means.

6. An artificial ventilator having a variable gas flow rate during a patient's inspiration or expiration comprising:
   input means for introducing flow rate information; and
   means, responsive to said flow rate information developed by said input means, for controlling the rate of said gas flow to match the flow rates introduced by said flow rate information;
   said input means introducing said flow rate information as a plurality of volumes distributed over the time of a single inspiration to allow introduction of time related flow rate information;
   said input means including a plurality of sliding volume selection means, disposed so as to slide in parallel patterns, for introducing said flow rate information, each said volume selection means introducing a volume for a particular time period of a said inspiration;
   each said volume selection means having an indicator, the position of which indicates the relative flow rate for its associated time period of said inspiration, the indicators of said volume selection means collectively forming points above a reference line defining a curve which represents the flow rate with respect to time of said flow rate information for said inspiration.

7. The ventilator of claim 6 wherein said indicators are levers of said flow rate selection means.

8. The ventilator of claim 6 further comprising:
   an inspiration gas circuit, said means for controlling varying the rate of gas flow within said inspiration gas circuit.

9. An artificial ventilator having a variable gas flow rate during a patient's inspiration or expiration comprising:

input means for introducing flow rate information; and means, responsive to said flow rate information developed by said input means, for controlling the rate of said gas flow to match the flow rates introduced by said flow rate information;

said input means introducing said flow rate information as a plurality of volumes distributed over the time of a single inspiration to allow introduction of time related flow rate information; and flow sensor means for monitoring the flow rate of an inspiration of a patient while the patient breathes unaided and wherein said flow rate information introduced by said input means is adjustable in accordance with the flow rate monitored by said flow sensor means.

* * * * *